(12) United States Patent
Tokime

(10) Patent No.: US 11,199,693 B2
(45) Date of Patent: Dec. 14, 2021

(54) CAMERA HEAD FOR ENDOSCOPE

(71) Applicant: Sony Olympus Medical Solutions Inc., Tokyo (JP)

(72) Inventor: Tetsuaki Tokime, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 2 days.

(21) Appl. No.: 16/713,051

(22) Filed: Dec. 13, 2019

(65) Prior Publication Data

US 2020/0285042 A1 Sep. 10, 2020

(30) Foreign Application Priority Data

Mar. 4, 2019 (JP) .............................. JP2019-038920

(51) Int. Cl.
*A61B 1/00* (2006.01)
*G02B 23/24* (2006.01)

(52) U.S. Cl.
CPC ..... *G02B 23/2484* (2013.01); *G02B 23/2415* (2013.01); *G02B 23/2461* (2013.01)

(58) Field of Classification Search
CPC ............ G02B 23/2484; G02B 23/2415; G02B 23/2461; A61B 1/127

USPC .................................. 359/656; 600/109, 169
See application file for complete search history.

(56) References Cited

U.S. PATENT DOCUMENTS 10,285,576 B2 * 5/2019 Ide ..................... A61B 1/00096

FOREIGN PATENT DOCUMENTS

JP 2015-134039 A 7/2015

\* cited by examiner

*Primary Examiner* — William Choi
(74) *Attorney, Agent, or Firm* — Xsensus LLP

(57) ABSTRACT

A camera head for an endoscope includes: a casing grasped by a user and detachably connected to an insertion unit inserted into a subject, the insertion unit taking an object image from the subject; an optical element having translucency and configured to seal the casing by being provided in the casing; an imaging element provided in the casing and configured to capture the object image taken into the casing through the optical element; and a dew condensation forming unit provided in the casing and having a smaller thermal resistance value than the optical element, the dew condensation forming unit functioning as a transmission path of heat between inside and outside of the casing.

15 Claims, 3 Drawing Sheets

CAMERA HEAD FOR ENDOSCOPE

This application claims priority from Japanese Application No. 2019-038920, filed on Mar. 4, 2019, the contents of which are incorporated by reference herein in its entirety.

BACKGROUND

The present disclosure relates to a camera head for an endoscope.

In the related art, a camera head for an endoscope to which camera head an insertion unit that is inserted into a subject such as a person (into living body) and that takes an object image from the subject is detachably connected, and which camera head captures the object image emitted from the insertion unit has been known (see, for example, Japanese Laid-open Patent Publication No. 2015-134039).

The camera head for an endoscope according to Japanese Laid-open Patent Publication No. 2015-134039 includes a casing to which an insertion unit is detachably connected, the casing being grasped by a user, an optical element that has translucency and that seals the casing by being provided in the casing, and an imaging element that is provided in the casing and that captures an object image taken into the casing through the optical element.

SUMMARY

Incidentally, in a case where a watertight structure in which intrusion of liquid from a gap into a casing is controlled by squashing of a rubber seal or the like is employed as the camera head for an endoscope according to Japanese Laid-open Patent Publication No. 2015-134039, there is a possibility that the following problem is generated.

In a case where washing and disinfection of the camera head for an endoscope are performed at high temperature by utilization of a washer disinfector that is one of reprocessing, there is a case where a minute amount of water vapor intrudes into the casing. Thus, in a camera head for an endoscope on which camera head the washing and disinfection are performed for a certain number of times or more, a water vapor amount in a casing is relatively large. Then, when a temperature in the casing is increased and a temperature difference is generated between the inside and the outside of the casing in the camera head for an endoscope, an optical element becomes a transmission path of heat inside and outside the casing. Thus, there is a problem that dew condensation is likely to be generated on the optical element. The optical element has a function of taking, into the casing, an object image emitted from an insertion unit. Thus, when dew condensation is generated on the optical element, observation of the inside of a living body is interrupted.

There is a need for a camera head for an endoscope which camera head may control dew condensation on an optical element.

According to one aspect of the present disclosure, there is provide a camera head for an endoscope, including: a casing grasped by a user and detachably connected to an insertion unit inserted into a subject, the insertion unit taking an object image from the subject; an optical element having translucency and configured to seal the casing by being provided in the casing; an imaging element provided in the casing and configured to capture the object image taken into the casing through the optical element; and a dew condensation forming unit provided in the casing and having a smaller thermal resistance value than the optical element, the dew condensation forming unit functioning as a transmission path of heat between inside and outside of the casing.

DETAILED DESCRIPTION

Figure 1:
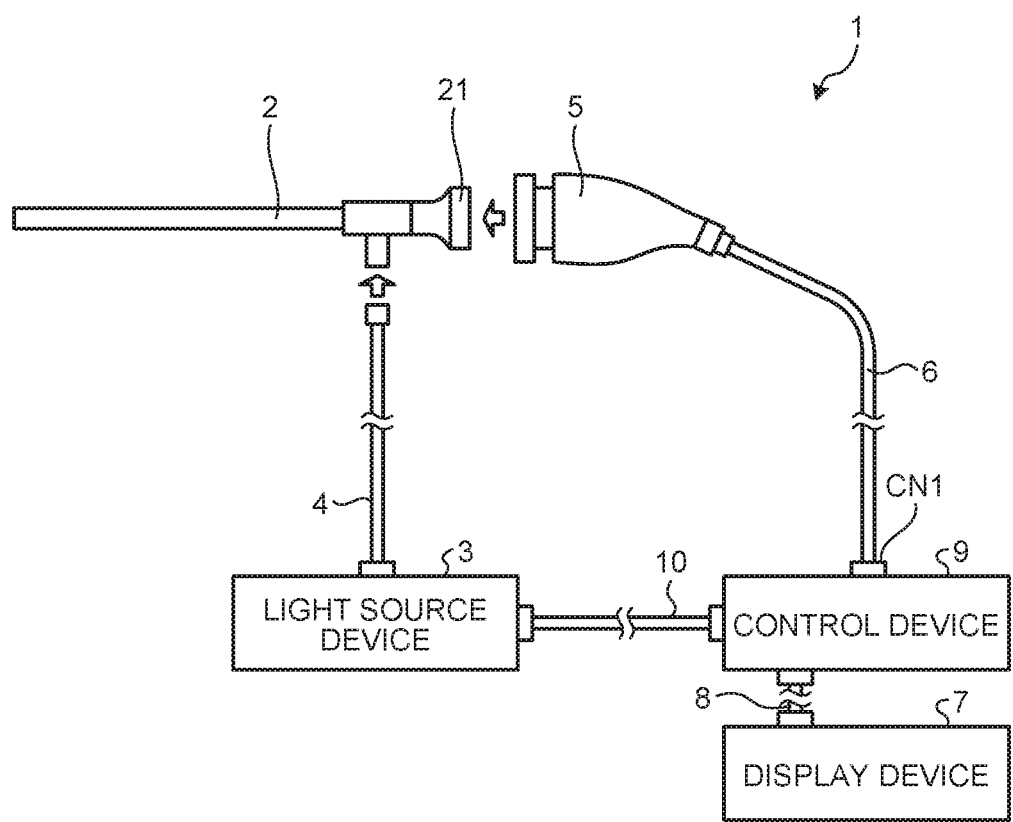
FIG. 1 is a view illustrating a schematic configuration of a medical observation system according to a first embodiment.

In the following, embodiments will be described with reference to the drawings. Note that the present disclosure is not limited by the embodiments described in the following. Also, in the drawings, the same sign is assigned to identical portions.

First Embodiment

Schematic Configuration of Medical Observation System

FIG. 1 is a view illustrating a schematic configuration of a medical observation system 1 according to the first embodiment.

The medical observation system 1 is a system that is used in a medical field and that observes the inside of a subject (inside of living body). As illustrated in FIG. 1, this medical observation system 1 includes an insertion unit 2, a light source device 3, a light guide 4, a camera head for an endoscope 5, a first transmission cable 6, a display device 7, a second transmission cable 8, a control device 9, and a third transmission cable 10.

In the first embodiment, the insertion unit 2 includes a rigid endoscope. That is, the insertion unit 2 has an elongated shape which is rigid as a whole or in which a part is flexible and the other part is rigid, and is inserted into a living body. In this insertion unit 2, an optical system that includes one or a plurality of lenses and that collects light from the inside of the living body (object image) is provided.

With one end of the light guide 4 being connected, the light source device 3 supplies light, which is to illuminate the inside of the living body, to the one end of the light guide 4 under control of the control device 9.

Note that in the first embodiment, the light source device 3 is configured separately from the control device 9. However, this is not a limitation, and a configuration in which a light source device 3 is provided in the control device 9 may be employed.

The one end of the light guide 4 is detachably connected to the light source device 3, and the other end thereof is detachably connected to the insertion unit 2. Then, the light guide 4 transmits the light supplied from the light source device 3 from the one end to the other end, and supplies the light to the insertion unit 2. The light supplied to the insertion unit 2 is emitted from a distal end of the insertion unit 2 into the living body. The light emitted into the living body and reflected on the inside of the living body (object image) is collected by the optical system in the insertion unit 2. The object image collected by the optical system in the insertion unit 2 is emitted from a proximal end of the insertion unit 2 (eyepiece unit 21 (FIG. 1)).

The insertion unit 2 (eyepiece unit 21) is detachably connected to the camera head for an endoscope 5. Then, under the control of the control device 9, the camera head for an endoscope 5 captures the object image emitted from the eyepiece unit 21 and outputs an image signal (RAW signal) by the imaging. For example, the image signal is an image signal of 4K or higher.

Note that a detailed configuration of the camera head for an endoscope 5 will be described later.

One end of the first transmission cable 6 is detachably connected to the control device 9 through a connector CN1 (FIG. 1), and the other end thereof is connected to the camera head for an endoscope 5. Then, the first transmission cable 6 transmits the image signal or the like output from the camera head for an endoscope 5 to the control device 9, and transmits a control signal, a synchronization signal, a clock, electric power, and the like output from the control device 9 to the camera head for an endoscope 5.

Note that in transmission of an image signal or the like from the camera head for an endoscope 5 to the control device 9 through the first transmission cable 6, the image signal or the like may be transmitted as an optical signal or may be transmitted as an electric signal. Transmission of a control signal, a synchronization signal, and a clock from the control device 9 to the camera head for an endoscope 5 through the first transmission cable 6 is in a similar manner.

The display device 7 includes a liquid-crystal or organic electro luminescence (EL) displaying display or the like, and displays an observation image based on a video signal from the control device 9 under control of the control device 9.

One end of the second transmission cable 8 is detachably connected to the display device 7, and the other end thereof is detachably connected to the control device 9. Then, the second transmission cable 8 transmits a video signal processed in the control device 9 to the display device 7.

The control device 9 includes a central processing unit (CPU) and the like, and integrally controls operations of the light source device 3, the camera head for an endoscope 5, and the display device 7.

For example, the control device 9 generates a video signal by performing various kinds of processing with respect to the image signal acquired from the camera head for an endoscope 5 through the first transmission cable 6, and outputs the video signal to the display device 7 through the second transmission cable 8. Then, the display device 7 displays an observation image based on the video signal. Also, the control device 9 outputs a control signal or the like to the camera head for an endoscope 5 or the light source device 3 through the first and third transmission cables 6 and 10.

One end of the third transmission cable 10 is detachably connected to the light source device 3, and the other end thereof is detachably connected to the control device 9. Then, the third transmission cable 10 transmits the control signal from the control device 9 to the light source device 3.

Configuration of Camera Head for Endoscope

Next, a configuration of the camera head for an endoscope 5 will be described.

Figure 2:
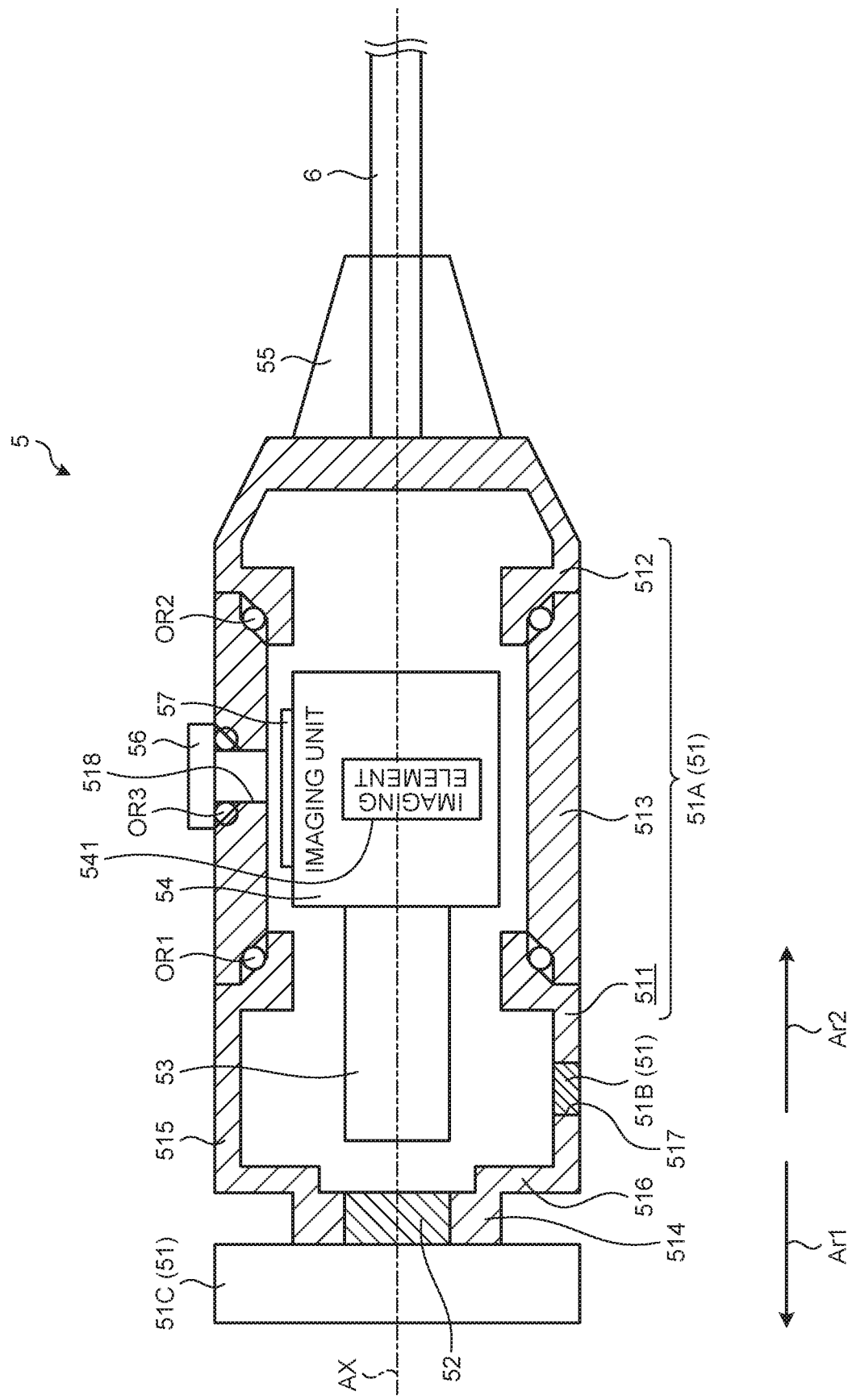
FIG. 2 is a view illustrating a camera head for an endoscope.

FIG. 2 is a view illustrating the camera head for an endoscope 5. More specifically, FIG. 2 is a sectional view in which the camera head for an endoscope 5 is cut along a plane including an optical axis Ax of an object image emitted from the eyepiece unit 21.

Note that in FIG. 2, a side to which the eyepiece unit 21 is connected is assumed as a distal end side Ar1, and a side to which the first transmission cable 6 is connected is assumed as a proximal end side Ar2 for convenience of description.

As illustrated in FIG. 2, the camera head for an endoscope 5 includes a casing 51, an optical element 52, a lens unit 53, an imaging unit 54, a proximal end sealing member 55, and an operating unit 56.

The casing 51 is a portion to which the insertion unit 2 (eyepiece unit 21) is detachably connected, and which is grasped by a user such as a doctor. As illustrated in FIG. 2, this casing 51 includes a casing main body 51A, a dew condensation forming unit 51B, and an attachment unit 51C.

The casing main body 51A includes a metal material such as stainless. As illustrated in FIG. 2, this casing main body 51A includes a first casing unit 511 placed on the distal end side Ar1, a second casing unit 512 placed on the proximal end side Ar2, and a middle casing unit 513 placed between the first and second casing units 511 and 512.

As illustrated in FIG. 2, the first casing unit 511 includes first and second tube units 514 and 515, and a connecting unit 516.

The first tube unit 514 is formed in a tubular shape (such as cylindrical shape), and is placed on the distal end side Ar1 of the second tube unit 515 and the connecting unit 516. Also, the first tube unit 514 holds an optical element 52 inside.

The second tube unit 515 is formed in a tubular shape (such as cylindrical shape) that has an inner shape size larger than an outer shape size of the first tube unit 514.

The connecting unit 516 is formed in a circular shape (such as annular shape), and connects the first and second tube units 514 and 515 to each other.

Then, the first and second tube units 514 and 515, and the connecting unit 516 are formed integrally in such a manner that central axes thereof become identical to the optical axis Ax.

The middle casing unit 513 is formed in a tubular shape (such as cylindrical shape), and is assembled to the first casing unit 511 in a state in which an end portion on the proximal end side Ar2 of the second tube unit 515 is fitted inside. Here, a sealing unit OR1 (FIG. 2) such as a rubber seal is arranged in a squashed state between the first casing unit 511 and the middle casing unit 513. That is, the first casing unit 511 and the middle casing unit 513 are watertightly sealed by the sealing unit OR1.

The second casing unit 512 is formed in a tubular shape (such as cylindrical shape), and is assembled to the middle casing unit 513 in a state in which an end portion on the distal end side Ar1 is fitted into the inside of the middle casing unit 513. Here, a sealing unit OR2 (FIG. 2) such as a rubber seal is arranged in a squashed state between the second casing unit 512 and the middle casing unit 513. That is, the second casing unit 512 and the middle casing unit 513 are watertightly sealed by the sealing unit OR2.

In the first embodiment, the dew condensation forming unit 51B is provided separately from the casing main body 51A. More specifically, for example, by brazing and soldering, the dew condensation forming unit 51B is fixed into a through hole 517 (FIG. 2) piercing through the second tube unit 515. That is, the through hole 517 is airtightly sealed by the dew condensation forming unit 51B.

Note that a function of the dew condensation forming unit 51B will be described later.

The attachment unit 51C is a portion to which the insertion unit 2 (eyepiece unit 21) is attached. This attachment unit 51C is formed in a bottomed tubular shape (such as bottomed cylindrical shape) that has an outer shape size larger than an outer shape size of the first tube unit 514 and that has an opening on the distal end side Ar1, and is fixed to an outer peripheral surface of the first tube unit 514 in a state in which the first tube unit 514 pierces through a bottom portion on the proximal end side Ar2. In this state, the connecting unit 516 faces the attachment unit 51C.

Then, the eyepiece unit 21 is fitted into the inside of the attachment unit 51C, whereby the insertion unit 2 is attached to the camera head for an endoscope 5.

The optical element 52 includes a material having translucency, and is fixed in the first tube unit 514, for example, by brazing and soldering. That is, the optical element 52 airtightly seals an opening on the distal end side An of the casing main body 51A (inside of first tube unit 514).

The lens unit 53 is provided in the casing main body 51A. Then, the lens unit 53 forms, on an imaging surface of the imaging unit 54 (imaging element 541), an object image emitted from the insertion unit 2 (eyepiece unit 21) and taken into the casing main body 51A through the optical element 52.

The imaging unit 54 is provided in the casing main body 51A and captures the inside of a living body under control of the control device 9. This imaging unit 54 includes an imaging element 541 such as a charge coupled device (CCD) or a complementary metal oxide semiconductor (CMOS) that receives the object image formed by the lens unit 53 and that performs conversion thereof into an electric signal, a signal processing unit (not illustrated) that performs signal processing (such as A/D conversion) with respect to the electric signal (analog signal) from the imaging element 541 and that outputs an image signal (RAW signal (digital signal)), and the like.

Then, the imaging unit 54 is electrically connected to the first transmission cable 6 that is wired in the casing main body 51A through an opening on the proximal end side Ar2 of the casing main body 51A (opening on proximal end side Ar2 of second casing unit 512).

The proximal end sealing member 55 is a member that watertightly seals a gap between the opening on the proximal end side Ar2 of the second casing unit 512 and an outer surface of the first transmission cable 6.

As illustrated in FIG. 2, the operating unit 56 includes a push-button switch or the like provided in such a manner as to be exposed to an outer surface of the middle casing unit 513 through a through hole 518 piercing through the middle casing unit 513, and receives operation by a user such as a doctor. Note that as illustrated in FIG. 2, a sealing unit OR3 such as a rubber seal is arranged in a squashed manner between the operating unit 56 and the through hole 518. That is, the operating unit 56 and the through hole 518 are watertightly sealed by the sealing unit OR3.

Then, as illustrated in FIG. 2, an operation board 57 on which a switch element (not illustrated) is mounted is provided in a position, which faces the operating unit 56, in the casing main body 51A.

Here, the operation board 57 is electrically connected to the first transmission cable 6 wired in the casing main body 51A through the opening on the proximal end side Ar2 of the second casing unit 512. That is, the operation board 57 (switch element) outputs an operation signal, which corresponds to pressing on the operating unit 56 by a user such as a doctor, to the control device 9 through the first transmission cable 6.

Function of Dew Condensation Forming Unit

Next, a function of the above-described dew condensation forming unit 51B will be described.

The dew condensation forming unit 51B has a function of controlling dew condensation on the optical element 52.

Incidentally, dew condensation becomes a transmission path of heat inside and outside the casing 51, and is likely to be generated in a place where heat is likely to pass. In other words, dew condensation is likely to be generated in a place where a thermal resistance value (thickness [m]/ thermal conductivity [W/(m·K)]) is small.

Then, the dew condensation forming unit 51B is set to have a smaller thermal resistance value than the optical element 52. That is, by preferential generation of dew condensation on the dew condensation forming unit 51B, dew condensation on the optical element 52 is controlled.

In the first embodiment, the dew condensation forming unit 51B includes the same material as the optical element 52 (such as sapphire glass) and has a smaller thickness dimension than the optical element 52, whereby it is set to have a smaller thermal resistance value than the optical element 52.

Also, the dew condensation forming unit 51B is provided on a side that faces the operating unit 56 with the optical axis Ax being therebetween (lower side in FIG. 2).

According to the first embodiment described above, the following effect is acquired.

In the camera head for an endoscope 5 according to the first embodiment, the dew condensation forming unit 51B includes the same material as the optical element 52 and has a smaller thickness dimension than the optical element 52, whereby it is set to have a smaller thermal resistance value than the optical element 52.

Thus, according to the camera head for an endoscope 5 of the first embodiment, it is possible to preferentially generate dew condensation on the dew condensation forming unit 51B, to control dew condensation on the optical element 52, and to observe the inside of a living body well.

Specifically, since the optical element 52 and the dew condensation forming unit 51B include the same material, brazing and soldering may be performed in the same process when the optical element 52 and the dew condensation forming unit 51B are fixed to the first casing unit 511 by brazing and soldering. Thus, it is possible to easily produce the camera head for an endoscope 5 compared to a case where an optical element 52 and a dew condensation forming unit 51B include different materials and brazing and soldering are performed in difference processes.

Also, in the camera head for an endoscope 5 according to the first embodiment, the dew condensation forming unit 51B is provided on the side that faces the operating unit 56 with the optical axis Ax being therebetween.

Incidentally, as a usage form of the camera head for an endoscope 5, the camera head for an endoscope 5 is often used in a posture in which the operating unit 56 is placed on an upper side. That is, when the camera head for an endoscope 5 is used, the dew condensation forming unit 51B is placed on a lower side of the camera head for an endoscope 5 at all times.

Thus, a movement of a water droplet, which is generated by dew condensation on the dew condensation forming unit 51B, to a different place in the casing 51 may be controlled. Specifically, since the dew condensation forming unit 51B is provided on the side that faces the operating unit 56 with the optical axis being therebetween, that is, provided in such a manner as to be separated from the operating unit 56, it is possible to control attachment of a water droplet, which is generated by the dew condensation on the dew condensation forming unit 51B, to the operation board 57.

Second Embodiment

Next, the second embodiment will be described.

Figure 3:
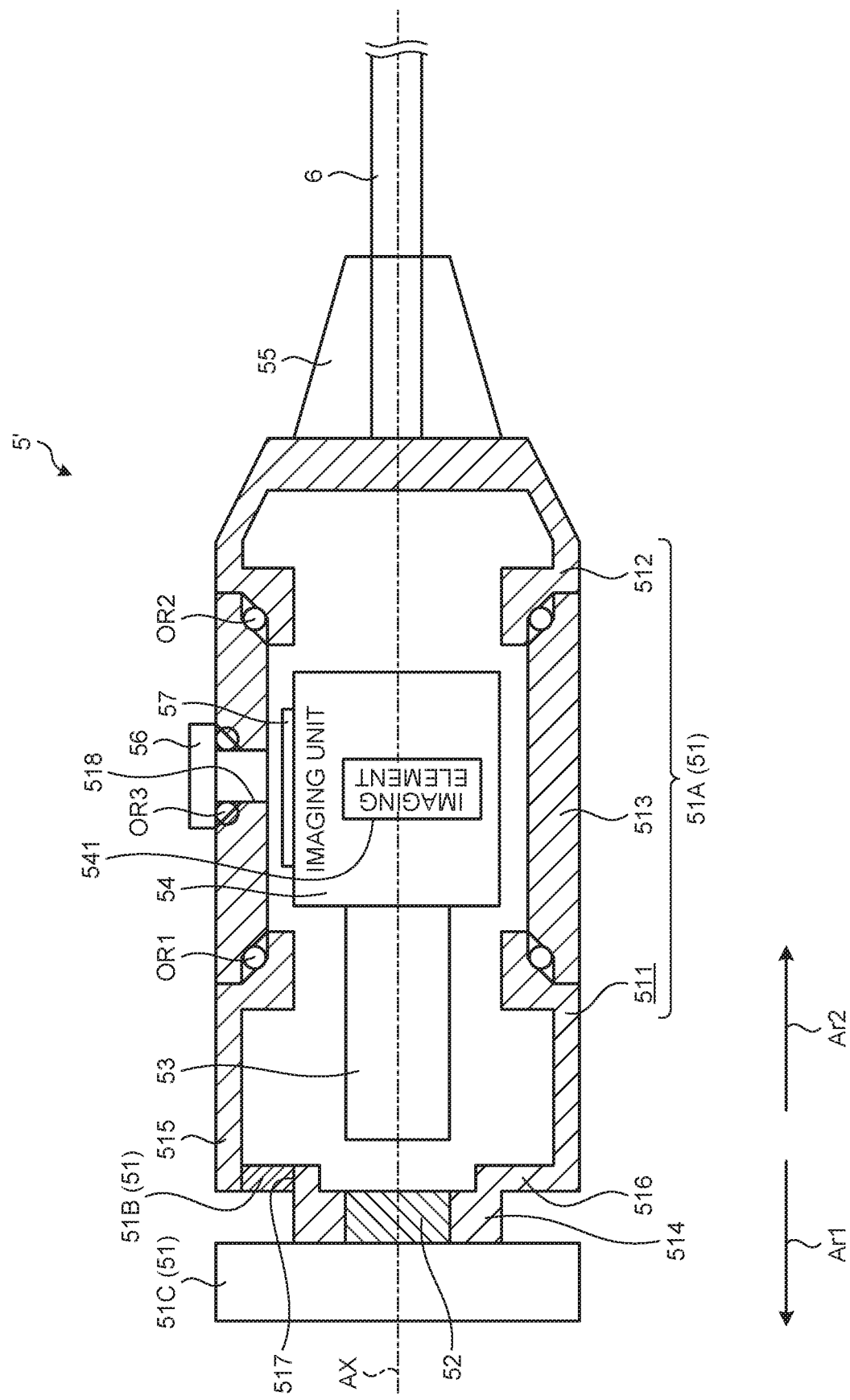
FIG. 3 is a camera head for an endoscope according to a second embodiment.

FIG. 3 is a view illustrating a camera head for an endoscope 5' according to the second embodiment. Note that FIG. 3 is a sectional view corresponding to FIG. 2.

As illustrated in FIG. 3, the camera head for an endoscope 5' according to the second embodiment is different from the above-described first embodiment only in a point that a position where a dew condensation forming unit 51B and a through hole 517 are provided is not in a second tube unit 515 but in a connecting unit 516. That is, in the camera head for an endoscope 5' according to the second embodiment, the dew condensation forming unit 51B is provided on a wall portion different from a wall portion where an operating unit 56 is provided in a casing 51.

According to the second embodiment described above, the following effect is acquired in addition to an effect similar to that of the above-described first embodiment.

Incidentally, when a user such as a doctor touches the dew condensation forming unit 51B and a temperature of the dew condensation forming unit 51B is increased, it is difficult to preferentially generate dew condensation on the dew condensation forming unit 51B.

Here, the connecting unit 516 faces an attachment unit 51C. Thus, the connecting unit 516 is a place where the user such as a doctor may not touch in the casing 51.

Then, in the camera head for an endoscope 5' according to the second embodiment, the dew condensation forming unit 51B is provided in the connecting unit 516 where the user such as a doctor may not touch. Thus, the temperature of the dew condensation forming unit 51B is not increased by a touch on the dew condensation forming unit 51B by the user such as a doctor, whereby it is possible to preferentially generate dew condensation on the dew condensation forming unit 51B and to control dew condensation on an optical element 52 efficiently.

Third Embodiment

Next, the third embodiment will be described.

In the following description, the same sign is assigned to a configuration similar to that of the above-described first embodiment, and a detailed description thereof is omitted or simplified.

The dew condensation forming unit 51B according to the above-described first embodiment includes the same material as the optical element 52 and has a smaller thickness dimension than the optical element 52, whereby it is set to have a smaller thermal resistance value than the optical element 52.

On the other hand, in the third embodiment, an optical element 52 includes a material having relatively low thermal conductivity (such as quartz glass). Then, a dew condensation forming unit 51B includes a material having higher thermal conductivity than the optical element 52 (such as sapphire glass) and is set to have a lower thermal resistance value than the optical element 52.

Even in a case where materials of the optical element 52 and the dew condensation forming unit 51B are different in a manner of the third embodiment described above, an effect similar to that of the above-described first embodiment is acquired.

Note that the optical element 52 and the dew condensation forming unit 51B according to the third embodiment may be employed in the camera head for an endoscope 5 according to the above-described second embodiment.

Different Embodiment

In the above, the embodiments have been described. However, the present disclosure should not be limited only to the above-described first to third embodiments.

In the above-described first to third embodiments, only one dew condensation forming unit 51B is provided. However, this is not a limitation, and a plurality of dew condensation forming units 51B may be provided.

In the above-described first to third embodiments, a casing main body 51A includes three bodies that are first and second casing units 511 and 512, and a middle casing unit 513. However, this is not a limitation, and two bodies may be included or four or more bodies may be included.

In the above-described first to third embodiments, a dew condensation forming unit 51B is configured separately from a casing main body 51A. However, this is not a limitation, and a dew condensation forming unit 51B may be formed integrally with a casing main body 51A in the same material. For example, when a part or a whole of a casing main body 51A has a smaller thermal resistance value than an optical element 52, the part or the whole of the casing main body 51A corresponds to a dew condensation forming unit according to the present disclosure.

In the above-described first to third embodiments, a dew condensation forming unit 51B is provided on a side that faces an operating unit 56 with an optical axis Ax being therebetween, or in a connecting unit 516. However, this is not a limitation, and provision to a different position is possible.

In the above-described first to third embodiments, a medical observation system 1 may be used not only in a medical field but also in an industrial field, and may be configured as a system that observes the inside of a subject such as a machine structure.

According to the camera head for an endoscope of the present disclosure, there is an effect that dew condensation on an optical element may be controlled.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A camera head for an endoscope, comprising:
   a casing grasped by a user and detachably connected to an insertion portion inserted into a subject, the insertion portion taking an object image from the subject;
   an optical element that is transparent and configure dto seal the casing by being provided in the casing;
   an imaging element provided in the casing and configured to capture the object image taken into the casing through the optical element; and
   a dew condensation forming unit provided in the casing and having a smaller thermal resistance value than the optical element, the dew condensation forming unit functioning as a transmission path of heat between inside and outside of the casing.

2. The camera head according to claim 1, wherein the casing includes:
   a casing main body; and
   the dew condensation forming unit provided separately from the casing main body.

3. The camera head for an endoscope according to claim 1, wherein the dew condensation forming unit is formed of same material as the optical element and has a smaller thickness dimension than the optical element.

4. The camera head according to claim 1, wherein the dew condensation forming unit is formed of a material having higher thermal conductivity than the optical element.

5. The camera head according to claim 1, further comprising an operating unit provided in such a manner as to be exposed to an outer surface of the casing and configured to receive operation by a user,
wherein the dew condensation forming unit is provided on a side that faces the operating unit with an optical axis of the object image incident on the imaging element being therebetween.

6. The camera head according to claim 1, further comprising an operating unit provided in such a manner as to be exposed to an outer surface of the casing and configured to receive operation by a user,
wherein the dew condensation forming unit is provided in a wall portion different from a wall portion where the operating unit is provided in the casing.

7. The camera head according to claim 1, wherein
the casing includes:
a casing main body; and
an attachment connected to the casing main body and detachably connected to the insertion portion,
the casing main body includes:
a first tube connected to the attachment and having a smaller size than the attachment in a cross section orthogonal to an optical axis of the object image incident on the imaging element:
a second tube at least a part of which having a larger size than the first tube in the cross section orthogonal to the optical axis: and
a connector configured to face the attachment and connect the first tube and the second tube, and
the dew condensation forming unit is provided in the connector.

8. A camera head for an endoscope, comprising:
a casing detachably connected to an insertion tube that collects light from an object;
a transparent portion that seals the casing;
a detector in the casing, the detector configured to capture an object image of the object transmitted from the insertion tube through the transparent portion; and
a dew condensation portion exposed to an side and an outside otthe casing, the dew condensation portion having a smaller thermal resistance value than the transparent portion.

9. The camera head according to claim 8, wherein the casing includes:
a casing main body; and
the dew condensation portion is separate from the casing main body.

10. The camera head for an endoscope according to claim 8, wherein the dew condensation portion is formed of same material as the transparent portion and has a smaller thickness than the transparent portion.

11. The camera head according to claim 8, wherein the dew condensation portion is formed of a material having higher thermal conductivity than the transparent portion.

12. The camera head according to claim 8, further comprising a control input exposed by the casing and configured to receive operation by a user,
wherein the dew condensation portion is provided on a side of the casing that faces the control input with an optical axis of the object image incident on the detector being therebetween.

13. The camera head according to claim 8, further comprising a control input exposed by the casing and configured to receive operation by a user,
wherein the dew condensation portion is provided in a wall of the casing different from a wall of the casing where the control input is located.

14. The camera head according to claim 8, wherein
the casing includes:
a casing main body; and
an attachment connected to the casing main body and detachably connected to the insertion tube,
the casing main body includes:
a first tube connected to the attachment and having a smaller size than the attachment in a cross section orthogonal to an optical axis of the object image incident on the detector:
a second tube at least a part of which having a larger size than the first tube in the cross section orthogonal to the optical axis: and.
a connector configured to face the attachment and connect the first tube and the second tube, and
the dew condensation portion is provided in the connector.

15. The camera head according to claim 8, wherein the dew condensation portion serves as a transmission path of heat between the inside and the outside of the casing.

* * * * *